United States Patent [19]

Cassar

[11] 4,058,605
[45] Nov. 15, 1977

[54] INSECTICIDES FROM DIMETHYLMUCONIC ACID

[75] Inventor: Richard D. Cassar, West Chester, Pa.

[73] Assignee: Sun Ventures, Inc., St. Davids, Pa.

[21] Appl. No.: 586,101

[22] Filed: June 11, 1975

[51] Int. Cl.² .......................... A01N 9/36; C07F 9/02
[52] U.S. Cl. .................................. 424/212; 424/205; 260/928; 260/942
[58] Field of Search ........................ 260/942; 424/212

[56] References Cited

U.S. PATENT DOCUMENTS

| | | | |
|---|---|---|---|
| 2,578,652 | 12/1951 | Cassaday | 424/212 |
| 3,431,325 | 3/1969 | Greenbaum | 424/212 |
| 3,883,618 | 5/1975 | Oswald et al. | 424/212 |

OTHER PUBLICATIONS

Chemical Abstracts, Vol. 74 (1971), p. 14099c.

*Primary Examiner*—V. D. Turner
*Attorney, Agent, or Firm*—Stanford M. Back; J. Edward Hess; Donald R. Johnson

[57] ABSTRACT

Novel compounds having the formula:

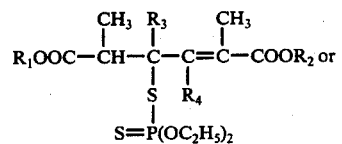

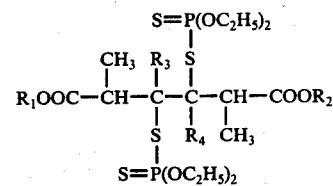

or mixtures thereof, wherein $R_1$ and $R_2$ are $C_{1-20}$ hydrocarbyl groups which may be the same or different, or one of $R_1$ and $R_2$ may be hydrogen, and $R_3$ and $R_4$ are methyl or hydrogen, and may be the same or different, can be prepared by the reaction of an alkyl ester, preferably the methyl ester, of polymethylmuconic acid with $(C_2H_5O)_2$ PSSH, the reaction product of ethanol and phosphorus pentasulfide.

6 Claims, No Drawings

INSECTICIDES FROM DIMETHYLMUCONIC ACID

BACKGROUND OF THE INVENTION

1. Field of the Invention

This invention relates to novel compositions of matter. More particularly it relates to a composition of matter having the formula:

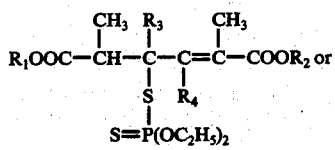

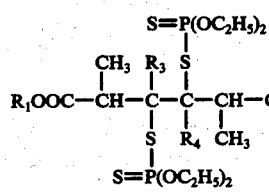

or mixtures thereof, wherein $R_1$ and $R_2$ are $C_{1-20}$ hydrocarbyl groups, as defined below, which may be the same or different, or one of $R_1$ and $R_2$ may be hydrogen, and $R_3$ and $R_4$ are methyl or hydrogen, and may be the same or different, which compositions are useful as insecticides. This invention also relates to the method of preparation of these polymethylmuconic acid derivative compounds as hereinabove defined.

2. Description of the Prior Art

It is well known that certain organothiophosphates have insecticide properties. The most widely used is Parathion (O,O-diethyl O-p-nitrophenyl thiophosphate) which is effective against a wider variety of insects than any known insecticide. However, it has a relatively short residual action and it is extremely toxic to humans. Malathion (O,O-dimethyl S-(1,2-dicarbethoxyethyl) dithiophosphate is less toxic to humans but hydrolyzes and isomerizes more easily, and therefore is less stable both in storage and as an insecticide residue. Thus, there exists a need for an effective insecticide agent that is not toxic to humans, yet is more persistant, i.e. remains on the treated area longer.

SUMMARY OF THE INVENTION

In accordance with the present invention, there are now provided novel compositions of matter having the formula:

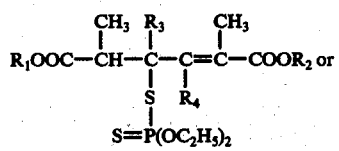

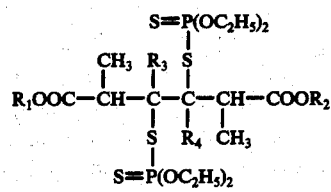

or mixtures thereof, wherein $R_1$ and $R_2$ are $C_{1-20}$ hydrocarbyl groups, as defined below, which may be the same or different, or one of $R_1$ and $R_2$ may be hydrogen, and $R_3$ and $R_4$ are methyl or hydrogen, and may be the same or different.

These compounds are prepared by the reaction of an alkyl ester of polymethylmuconic acid with $(C_2H_5O)_2$ PSSH, the reaction product of ethanol and phosphorus pentasulfide. These compositions are useful not only as insecticides, but also as plasticizers and softeners in resins and plastics.

DESCRIPTION OF THE INVENTION

The polymethylated muconic acid esters suitable for use in preparing the novel compositions disclosed herein are the $C_1$ to $C_{20}$ hydrocarbyl mono- and diesters of the acids wherein the hydrocarbyl group may contain from 1–20 carbon atoms, as well as any mixtures thereof or mixed esters.

The $C_1$–$C_{20}$ hydrocarbyl esters include those derived from hydrocarbyl radicals of $C_1$–$C_{20}$ hydrocarbons having acyclic, alicyclic, and aromatic structures such as those disclosed in the text "Handbook of Hydrocarbons", Ferris, S. W. Academic Press, Inc., New York, N. Y., (1955), pages 145–249, all of which are incorporated herein by reference. The preferred esters suitable for use in preparing the novel compositions of the present invention are the $C_1$–$C_{10}$ hydrocarbyl monoand diesters of the polymethylated muconic acids disclosed above. Examples of the $C_1$ to $C_{10}$ hydrocarbyl groups include methyl, ethyl, butyl, pentyl, hexyl, heptyl, octyl, nonyl, decyl cyclopentyl, methyl cyclopentyl, dicyclopentyl, cyclohexyl, phenyl, tolyl, xylyl, naphthyl, tetrahydronaphthyl, decahydronaphthyl, as well as the various isomers of each.

As aforestated, the diester of the meconic acid can be a mixed ester. An illustrative example is the cis-cis isomer of $\alpha,\alpha'$-dimethylmuconic acid which can be illustrated by the following structural formula:

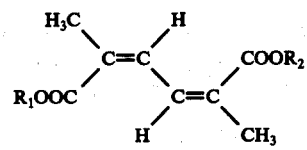

wherein $R_1$ is different from $R_2$. That is to say, $R_1$ can be a hydrocarbyl group of $C_1$ to $C_{20}$ and $R_2$ can be a different hydrocarbyl group of $C_1$ to $C_{20}$, e.g., $R_1$ may be cyclohexyl ($C_6$) while $R_2$ is eicosyl ($C_{20}$).

Examples of some of the esters of the polymethylated muconic acids suitable for use in the compositions of the present invention include the cis-cis, cis-trans and trans-trans isomers of the mono- and di-methyl esters of $\alpha,\beta'$-dimethylmuconic acid; the mono- and di-phenyl esters of $\alpha,\alpha',\beta,\beta'$-tetramethylmuconic acid; the mono- and dinaphthyl esters of $\alpha,\beta,\beta'$-trimethylmuconic acid; the mono- and di- 5,6-diethylacenaphthyl esters of $\alpha,\alpha'$-dimethyl-munconic acid; the mono- and di-cyclohexyl ester of $\alpha,\alpha'$-dimethylmuconic acid; the mono- and di-1,2-dimethylcycloheptyl esters of $\alpha,\beta'$-dimethylmuconic acid; the mono- and di-decahydronaphthyl esters of $\alpha,\alpha',\beta,\beta'$-tetramethylmuconic acid; the mono- and di-1,3-dipropylbenzyl esters of $\alpha,\alpha'$-dimethylmunconic acid; the mono- and di-2,9-dimethyl-4,7-diisobutyldecyl esters of $\alpha,\alpha',\beta$-trimethylmuconic acid; and the mono- and di-anthracyl esters of $\alpha,\beta'$-dimethylmuconic acid; mono- and di-2,6,10-trimethyl decyl esters of $\alpha,\alpha',\beta,\beta'$- tetramethylmuconic acid; and the nonyl ethyl esters of α,α'-tetramethylmunconic acid.

As noted above, polymethylated muconic acids can exist in three isomeric forms, viz., cis-cis, trans-trans and cis-trans. As an example, the unsaturated diacid, α,α'-dimethylmuconic acid, can be depicted by the following structural formulas:

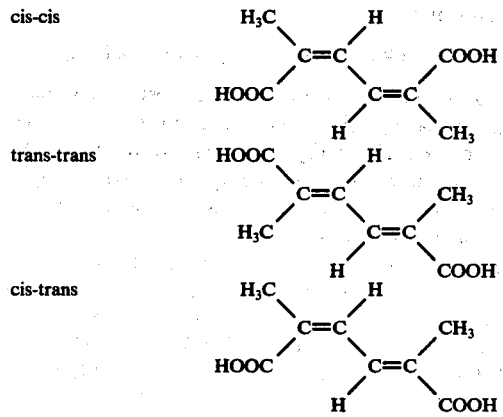

The preparation of each of these isomeric forms of the α,α'-dimethylmuconic acid has been described in the prior art by Elvidge et al., J. Chem. Soc., pp. 1026–1033 (1952). These authors show that oxidation of p-xylenol by means of peracetic acid gave the cis-cis form of the acid. The other isomeric forms were obtained indirectly by conversion of the cis-cis form. Also dimethyl esters of each of the three isomeric forms were prepared by shaking the respective DMMA with etheral diazomethane.

The cis-cis form of polymethylated muconic acids can also be obtained by biological oxidation of p-xylene utilizing special strains of microorganisms as disclosed in U.S. Pat. No. 3,383,289 issued May 14, 1968 of Raymond et al.

For purposes of this invention, it has been found that when the cis,cis-isomer is employed as the starting material, the product is the compound having the structural formula:

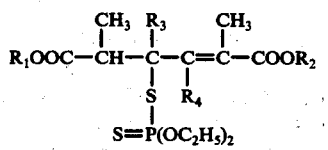

wherein $R_1$, $R_2$, $R_3$ and $R_4$ are as defined above, while the trans-trans-isomer provides the compound:

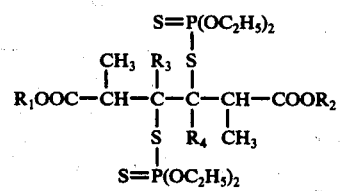

wherein $R_1$, $R_2$, $R_3$ and $R_4$ are as defined above. The cis-trans-isomer on the other hand, provides mixtures of both.

A convenient method for preparing the novel dithiophosphate derivatives of the aforedescribed muconic acid esters is simply to react the desired ester with diethyl dithiophosphate at an elevated temperature, desirably from 50°–150° C, preferably at about 70°–90° C, for about 18 to 30 hours. Suitable amounts of an oxidation inhibitor such as hydroquinone are desirably employed. The reaction product, after cooling, is then solvent extracted, e.g. with benzene, neutralized with an aqueous solution of sodium carbonate or the like, dried, and the solvent removed under vacuum to yield the dithiophosphate derivative.

When the cis,cis-acid ester isomer is employed, it will be seen that the mole ratio of this compound to acid should be about 1:1, preferably about 1.25:1 in order to maintain a slight excess of dithiophosphate. On the other hand, the trans,trans-acid ester isomer will require a 2:1 ratio of this compound to acid ester, preferably about 2.4:1, to maintain a stoichiometric balance.

As one means of illustrating the present invention the following examples are presented:

EXAMPLE 1

To 59.4 g of cis,cis-dimethylmuconic acid dimethyl ester is added 37.6 g of diethyl dithiophosphate and 0.2 g of hydroquinone. The reaction mixture is heated at 75° C for 24 hours, cooled to room temperature, and mixed with 200 ml of benzene. The solution is then water-washed with a 10% solution of sodium carbonate, the resulting organic layer dried with MgSO₄ and thereafter concentrated under vacuum to remove the benzene. The residue comprises the product:

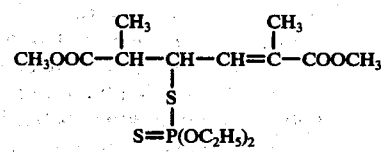

In accordance with the foregoing procedure, but substituting cis-cis dimethylmuconic acid ethyl ester for the corresponding dimethyl ester, there is obtained the compound:

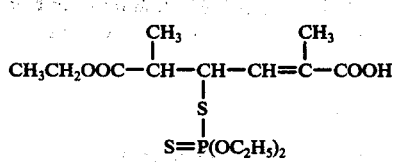

EXAMPLE 2

To 59.4 g trans,trans-dimethylmuconic acid dimethyl ester is added 75.2 g of diethyl dithiophosphate and 0.2 g of hydroquinone. The reaction mixture is heated at 85° C for 20 hours, cooled to room temperature, and mixed with 200 ml of benzene. The solution is then water-washed with a 10% solution of sodium carbonate, the resulting organic layer dried with MgSO₄, and thereafter concentrated under vacuum to remove the benzene. The residue comprises the product:

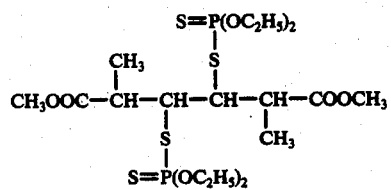

In accordance with the foregoing procedure, but substituting trans,trans-dimethylmuconic acid methyl ethyl diester for the corresponding dimethyl ester, there is obtained the compound:

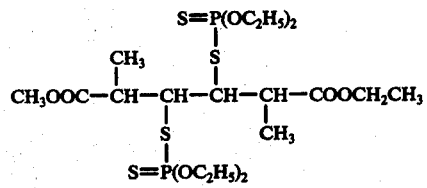

Also according to this invention there is provided a novel insecticide composition having as at least one of its essential active ingredients each of the muconic acid ester isomers enumerated above. According to the invention, when these esters are admixed with, compounded with or dissolved in a suitable liquid or solid carrier in amounts of 1 to 30 percent by weight based on the total weight of the composition, they are effective for killing insects.

For example, a 5% solution of any one of the abovedefined muconic acid esters dissolved in 5–15% methyl ethyl ketone or acetone, or the like, the balance consisting of petroleum spirits, when tested against the common housefly using the Standard Peet Grady method, provides a substantial kill of the total number of flies as compared with the Official Test Insecticide. Alternatively, a solid carrier such as a wettable clay may be employed in the above composition.

A test of methyl ethyl ketone and petroleum spirits indicates that the insecticidal efficacy of the composition of the invention is primarily due to the muconic acid esters, and not these solvents.

The invention claimed is:

1. A compound having the formula:

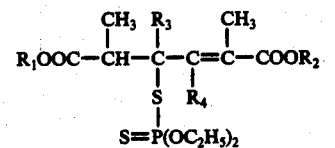

wherein $R_1$ and $R_2$ are methyl, or ethyl, and may be the same or different, or one of $R_1$ and $R_2$ may be hydrogen, and $R_3$ and $R_4$ are methyl or hydrogen, and may be the same or different.

2. A compound having the formula:

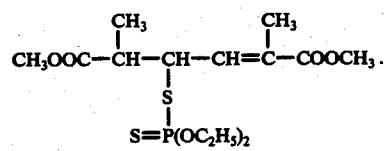

3. A compound having the formula:

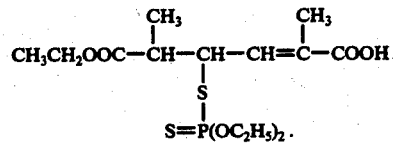

4. An insecticidal composition comprising a minor amount of an insecticidal compound having the formula:

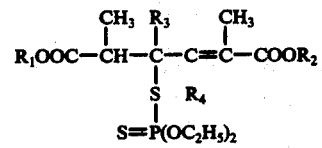

wherein $R_1$ and $R_2$ are methyl, or ethyl, and may be the same or different, or one of $R_1$ and $R_2$ may be hydrogen, and $R_3$ and $R_4$ are methyl or hydrogen, and may be the same or different, and a major amount of a suitable carrier.

5. The composition of claim 4 wherein the insecticidal compound comprises from about 1 to 30 weight percent of the total weight of the composition.

6. The composition of claim 4 wherein the insecticidal compound is:

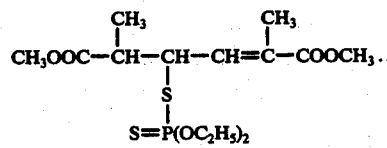

* * * * *